United States Patent [19]

Eibl et al.

[11] Patent Number: 5,410,022
[45] Date of Patent: Apr. 25, 1995

[54] METHOD OF PRODUCING A FACTOR VIII PREPARATION

[75] Inventors: Johann Eibl; Friedrich Elsinger; Herbert Gritsch; Yendra Linnau; Otto Schwarz; Peter Turecek, all of Vienna; Günther Wöber, Oberwaltersdorf, all of Austria

[73] Assignee: Immuno Aktiengesellschaft, Vienna, Austria

[21] Appl. No.: 49,585

[22] Filed: Apr. 20, 1993

[30] Foreign Application Priority Data

Apr. 24, 1992 [AT] Austria .................................. 849/92

[51] Int. Cl.$^6$ ..................... C07K 3/20; C07K 15/06
[52] U.S. Cl. ..................... 530/383; 530/417; 530/830; 530/831; 435/236
[58] Field of Search ............... 530/383, 830, 831, 417; 514/8, 21; 424/530; 435/236

[56] References Cited

U.S. PATENT DOCUMENTS

| 3,920,625 | 11/1975 | Anderson et al. | 530/350 |
|---|---|---|---|
| 4,160,025 | 7/1979 | Eibl et al. | 424/101 |
| 4,297,344 | 10/1981 | Schwinn et al. | 424/101 |
| 4,379,085 | 4/1983 | Williams | 424/101 X |
| 4,404,187 | 9/1983 | Schwinn et al. | 424/101 |
| 4,405,603 | 9/1983 | Schwinn et al. | 424/101 |
| 4,640,834 | 2/1987 | Eibl et al. | 424/94 |
| 4,673,733 | 6/1987 | Chandra et al. | 530/344 |
| 4,814,435 | 3/1989 | Schwarz et al. | 530/383 |
| 4,904,641 | 2/1990 | Eibl et al. | 514/2 |
| 4,909,251 | 3/1990 | Seelich | 606/213 |
| 5,043,428 | 8/1991 | Heimburger et al. | 530/383 |
| 5,118,794 | 4/1992 | Grangeorge et al. | 530/363 |
| 5,143,838 | 9/1992 | Kraus et al. | 435/214 |
| 5,186,945 | 2/1993 | Shanbrom | 424/529 |
| 5,252,709 | 10/1993 | Burnouf et al. | 530/382 |

FOREIGN PATENT DOCUMENTS

| 350726 | 6/1979 | Austria . |
|---|---|---|
| 390801 | 7/1990 | Austria . |
| 391808 | 12/1990 | Austria . |
| 2183/91 | 11/1991 | Austria . |
| 0015055 | 9/1980 | European Pat. Off. . |
| 0035204 | 9/1981 | European Pat. Off. . |
| 0050061 | 4/1982 | European Pat. Off. . |
| 0052827 | 6/1982 | European Pat. Off. . |
| 0053338 | 6/1982 | European Pat. Off. . |
| 0007870 | 5/1983 | European Pat. Off. . |
| 0094611 | 11/1983 | European Pat. Off. . |
| 0099445 | 2/1984 | European Pat. Off. . |
| 0117064 | 8/1984 | European Pat. Off. . |
| 0124044 | 11/1984 | European Pat. Off. . |
| 0124506 | 11/1984 | European Pat. Off. . |
| 0131740 | 1/1985 | European Pat. Off. . |
| 0142059 | 5/1985 | European Pat. Off. . |
| 0144709 | 6/1985 | European Pat. Off. . |
| 0159311 | 10/1985 | European Pat. Off. . |
| 0173242 | 3/1986 | European Pat. Off. . |
| 0177836 | 4/1986 | European Pat. Off. . |
| 0196761 | 10/1986 | European Pat. Off. . |
| 0197554 | 10/1986 | European Pat. Off. . |
| 02789487 | 8/1988 | European Pat. Off. . |

(List continued on next page.)

OTHER PUBLICATIONS

Burnouf-Radosevich, M. et al., "Chromatographic Preparation of a Therapeutic Highly . . . ", Vox Sang, vol. 62, pp. 1–11, 1992.

(List continued on next page.)

Primary Examiner—Michael G. Wityshyn
Assistant Examiner—C. Sayala
Attorney, Agent, or Firm—Foley & Lardner

[57] ABSTRACT

The invention relates to a method of producing virus-safe highly purified factor VIII. The method includes a combination of the following measures:

a) chromatographic purification of a factor VIII-containing fraction,
b) tenside treatment of factor VIII in an aqueous solution at a tenside/protein ratio of from 1:1 to 1000:1, and
c) heat treatment of the factor VIII preparation in the solid state.

26 Claims, No Drawings

OTHER PUBLICATIONS

| | | |
|---|---|---|
| 0292003 | 11/1988 | European Pat. Off. . |
| 0324729 | 7/1989 | European Pat. Off. . |
| 0341103 | 11/1989 | European Pat. Off. . |
| 0343275 | 11/1989 | European Pat. Off. . |
| 0345246 | 12/1989 | European Pat. Off. . |
| 1527261 | 12/1989 | European Pat. Off. . |
| 0378208 | 7/1990 | European Pat. Off. . |
| 0439156 | 7/1991 | European Pat. Off. . |
| 0519901 | 12/1992 | European Pat. Off. . |
| 0528701 | 2/1993 | European Pat. Off. . |
| 0534812 | 3/1993 | European Pat. Off. . |
| 0541507 | 5/1993 | European Pat. Off. . |
| 2916711 | 11/1980 | Germany . |
| 82/03871 | 11/1982 | WIPO . |
| 83/04371 | 12/1983 | WIPO . |
| 88/08710 | 11/1988 | WIPO . |
| WO90/15613 | 12/1990 | WIPO . |

FOREIGN PATENT DOCUMENTS

Burnouf, T. et al., "A Highly Purified Factor VIII: C concentrate . . . ", Vox Sang, vol. 60, pp. 8–15, 1991.

Prince, A. M., et al. "The development of virus–free Labile . . . ", Eur. J. Epidemiol., vol. 3 (2), pp. 103–118, 1987.

Schwinn, H. et al., "Progress in purification of virus–inactivated Factor VIII . . . ", Arzeneimi Helforschung, 39(10), pp. 1302–1305, 1989 Medline AN 90121338.

Mannucci, P. M. et al., "Outbreak of Hepatitis A Among Italian Patients with Haemophilia", *The Lancet*, vol. 339: p. 819 (Mar. 28, 1992).

Mannucci, P. M. et al., "Low Risk of Viral Infection After Administration of Vapor–Heated Factor VIII Concentrate", *Transfusion*, vol. 32: pp. 134–138 (1992).

Müller, W., "New Ion Exchangers for the Chromatography of Biopolymers", *Journal of Chromatography*, 510, pp. 133–140 (1990).

Directive EC III/8115/89–EN, Commission of the European Community.

Brummelhuis, H. G. J., "Preparation of the Prothrombin Complex", *Methods of Plasma Protein Fractionation*, pp. 117–125 (1980).

Pape, W. J. W. et al., "Standardization of an in vitro Red Blood Cell Test for Evaluating the Acute Cytotoxic Potential of Tensides", *Arzneim.–Forsch./Drug Res.* 40., pp. 498–502 (1990).

Vogelaar, E. F., "Contributions to the Optimal Use of Human Blood", *Vox Sanguinis*, vol. 26, pp. 118–127 (1974).

Hartert, H., "Thombosis and Bleeding Disorders", Academic Press, New York pp. 70–76 (1971).

Seelich, T., "Fibrinogen, Fibrin and Fibrin Glue, Side Effects of Therapy with Clotting Factor Concentrates", F. K. Schattauer Verlag, Stuttgart, New York pp. 199–208 (1980).

Suomela, H., "Preparation and Properties of a Therapeutic Factor IX Concentrate", *Vox Sanguinis, Journal of Blood Transfusion, Immunohaemotology and Immunopathology*, vol. 33, pp. 37–50 (1977).

Rubinstein, D. B., M.D., "Inability of Solvent–Detergent (S–D) Treated Factor VIII Concentrate to Inactivate Parvoviruses . . . ", *American Journal of Hematology* 35:142 (1990).

Chemical Abstracts, vol. 111, No. 22, 201439j, Nov. 27, 1989.

Chemical Abstracts, vol. 114, No. 5, 39082a, Feb. 4, 1991.

Rozenberg, XII International Congress on Blood Transfusion Abstracts, Moscow, pp. 473–475 (Aug. 17–23, 1969).

Chemical Abstracts, Pharmaceuticals, vol. 84, No. 16, 111640n, Apr. 19, 1976.

METHOD OF PRODUCING A FACTOR VIII PREPARATION

The invention relates to a method of producing virus-safe highly purified factor VIII.

The coagulation of blood is triggered by a series of sequential reactions of various proteins and enzymes. If there is a lack of blood coagulation factors, the formation of fibrin from fibrinogen and, thus, the sealing of wounds are prevented; hence result bleedings. Such is the case with hemophilia A. The latter is the most frequent disease with a tendency to hemorrhage and is caused by factor VIII deficiency. Factor VIII is present in plasma commonly with von Willebrand factor (vWF) as a non-covalently bound complex (FVIII/vWF). The proteins FVIII and vWF as well as the complex FVIII/vWF are used in the substitution treatment of hemophiliacs. Great demands are made on relevant pharmaceutical preparations with regard to efficiency and safety.

The starting material for the production of such preparations usually is human plasma, which, however, contains factor VIII only in slight amounts (approximately 0.1 to 0.2 $\mu$g/ml). Consequently, not only large amounts of plasma must be processed to recover factor VIII, but also interfering accompanying proteins must be separated as far as possible, many of these accompanying proteins having similar physico-chemical properties.

Another difficulty consists in that the preparation must be inactivated also in respect of infectious agents, since the starting material may contain, for instance, hepatitis virus or HIV. Add to this that each individual method step and each inactivation procedure must be carried out in a manner that the biologic activity of the coagulation factors sought must be preserved to the largest extent possible.

With classical production methods, stepwise precipitations (e.g., cryoprecipitation or precipitations by the addition of ammonium sulfate) are applied, whose purposes reside in the elimination of contaminations, such as prothrombin complex factors, fibrinogen and fibronectin. The purity of the factor VIII concentrates obtained is about 1 U/mg protein, usually not exceeding the limits of 10 to 20 U/mg protein.

From EP-A-0 378 208 a method for the production of factor VIII is known, according to which a cryoprecipitate solution is subjected to a treatment with an organic solvent (Tri-(n-butyl)phosphate (TNBP)) in the presence of the solubilizer Tween ® 80 for virus inactivation. Factor VIII subsequently is subjected to a two-step purification precipitation, is lyophilized and is heated in the dry state.

The treatment of biologic and pharmaceutical products with 0.25 to 10% by weight of a non-denaturating amphiphilic (detergent) is described in EP-B-0 050 061.

The method of treating proteins with organic solvents, if desired in the presence of detergents, is known from EP-B-0 131 740. There, it has been shown that treatment with a detergent alone is relatively ineffective in respect of virus inactivation. However, organic solvents only are active against viruses that are enveloped by membranes. Hepatitis infections have already occurred which are associated with factor VIII concentrates contaminated with hepatitis A and virus-inactivated in that manner. Hepatitis A virus does not have a lipid-containing membrane; as a result, it is not inactivated (Manucci P. M. et al. (1992) The Lancet 339, 819 ("Outbreak of Hepatitis A Among Italian Patients with Haemophilia").

The treatment of factor VIII-containing fractions with organic solvents usually is carried out in that the toxically active solvent must be separated after treatment in a cumbersome manner. In EP-A-0 343 275, the extraction of factor VIII-containing fractions with oils, such as soybean oil or caster oil, has been proposed for this purpose. After this, factor VIII is subjected to gel permeation chromatography on ion exchange materials.

According to the method of EP-A-0 094 611, factor VIII is heated in the dry state to reduce infectiousness.

According to EP-B-0 159 311, blood products are heated in the solid moist state to inactivate potentially present viruses. No case of infection has been reported in respect of such a "vapor-heated" factor VIII concentrate (Manucci P.M. (1992) Transfusion 32, 134–138 "Low Risk of Viral Infection After Administration of Vapor-Heated Factor VIII Concentrates").

Heat-treating highly purified factor VIII concentrates is considered critical. According to EP-A0 173 242, for instance, a mixture of stabilizers (carbohydrates and aminoacids) must be added to chromatographically purified factor VIII before the latter is heated in solution. Otherwise it has been common to subject the factor VIII-containing fraction to a virus inactivation treatment prior to chromatographic purification.

The invention has as its object to provide a method by which purified factor VIII can be produced that is considered virus-safe on account of an effective treatment for virus inactivation.

Preferably, the specific activity of the preparation produced is to be at least 25 U/mg protein.

In accordance with the invention, this object is achieved by a combination of the following measures:
a) chromatographic purification of a factor VIII-containing fraction,
b) tenside treatment of factor VIII in an aqueous solution at a tenside/protein ratio of from 1:1 to 1000:1, and
c) heat treatment of the factor VIII preparation in the solid state.

According to the invention, factor VIII may be produced as a FVIII/vWF complex, as FVIII or as vWF. During the production process, a treatment for the dissociation of FVIII/vWF complex is feasible, e.g., by calcium chloride.

It was found that the tenside treatment according to the invention surprisingly can be a successful virus inactivation. Non-ionic tensides, such as Tween ® 80, Triton ®X-100, Triton ®X-114, dodecyl maltoside or octyl glucoside, zwitterionic tensides, such as dimethyl octyl amine-N-oxide or N-dodecyl-N,N-dimethyl-3-ammonio-1-propane sulfonate, and ionic tensides, such as sodium deoxycholate or sodium cholate may, for instance, be used as tensides. The tenside treatment primarily is carried out in an aqueous solution free of organic solvents. A cryoprecipitate solution may be employed as the aqueous solution, which, if desired, additionally has been purified by adsorption of the prothrombin complex factors. In such a solution, a tenside/protein ratio of from 1:1 to 10:1 is preferred.

Preferably, the tenside treatment is carried out prior to chromatographic purification, preferably at a tenside/protein ratio of from 3.5:1 to 10:1, the tenside being separable in a simple manner during chromatography.

In another embodiment, the tenside treatment also is feasible during chromatography. This variant has the advantages of factor VIII being adsorbed in a specific manner even in the presence of proteins tending to aggregation and, thus, to undesired coadsorption.

If factor VIII is recovered from a starting material having a low protein content, it is usually suitable to maintain a defined tenside concentration within the aqueous solution. In this manner, the tenside/protein ratio may amount up to 1000:1.

A cell culture supernatant containing recombinant factor VIII, for instance, has a protein content of at least approximately 100 mg/l. A 10% tenside concentration in this cell culture supernatant, therefore, corresponds to a tenside/protein ratio of no more than approximately 1000:1.

To increase the safety against an infection by viruses not enveloped by membranes, the combination according to the invention with the heat treatment of factor VIII in the solid state is proposed. This may be realized on the lyophilized preparation, the heat treatment, preferably, being effected in the moist state of the preparation.

A preferred embodiment of the invention, therefore, also comprises heat treatment with hot vapor, wherein the factor VIII preparation in the solid state is adjusted to a content of water, methanol or ethanol of above 0.05 (5% by mass) and below 0.70 (70% by mass), preferably below 0.40 (40% by mass), and is heated in a closed container, if desired, in the presence of an inert protective gas, at a temperature ranging between 50° and 121° C.

The factor VIII lyophilisate additionally may contain albumin and/or salts, such as sodium citrate and/or aminoacids.

It has been shown in a surprising manner that this heat treatment does not involve a substantial loss of activity, for which reason it is also possible to treat relatively instable highly purified factor VIII.

During chromatographic purification, factor VIII is largely freed from accompanying proteins. A preferred embodiment of the production process comprises multistep chromatographic purification, wherein an adsorption material for factor VIII is employed in one step and a material for the adsorption of contaminating proteins is used in a further step.

Thus, an anion exchanger may, at first, be used for the adsorption of factor VIII and a material exhibiting a high affinity for fibronectin, such as gelatin or heparin, immobilized on an insoluble carrier may subsequently be used. In this case, chromatography in the presence of tensides also may be advantageous with a view to minimizing the unspecific adsorption of factor VIII on the affinity carrier.

To produce an albumin-free factor VIII preparation, adsorption of the factor VIII-containing solution may be effected on dye ligand gels (Cibacron ®-Blue 3GA, immobilized on an insoluble carrier (Bio-Rad); Fractogel ® TSK-AF-Blue (Merck), Blue-Sepharose ®CL6B (Pharmacia)).

Such gels are capable of binding albumin with a high selectivity; albumin cannot be quantitatively separated from factor VIII by other methods and constitutes an impurity in factor VIII preparations unless an albumin content is desired for stabilization.

For chromatographic purification, anion exchangers based on acrylates, silicates or carbohydrates, such as DEAE-Sephadex ® (Pharmacia), QAE-Sepharose ® (Pharmacia), DEAE-Toyopearl ® (Tosohaas), TMAE-Fractogel ® (Merck) and the like, are preferred.

Acrylate-based anion exchangers preferably are formed as a "tentacular matrices" (cf. Müller W (1990) Journal of Chromatography 510, 133–140 "New Ion Exchangers for the Chromatography of Biopolymers"). With such a matrix, the exchanger groups are located along a polymer side chain connected with the surface of the matrix. Hence result a high loading capacity and an improved selectivity.

The blood coagulation factor VIII produced according to the method of the invention is regarded as virus-safe and preferably exhibits a high specific activity of at least 25 U/mg protein.

The invention will be explained in more detail by way of the following examples.

Example 1

1 kg cryoprecipitate obtained from 101 liter plasma was dissolved in 3.5 liter buffer 1, i.e., a tris-lysine buffered NaCl solution (85 mmol/l).

To prepurify the factor VIII-containing solution, $Al(OH)_3$ was stirred in, $Al(OH)_3$ was separated, $BaSO_4$ was stirred in and then separated. After this, the pH of the supernatant was adjusted to 6.5, the temperature was lowered to 4° C. and the precipitate formed was separated by centrifugation and discarded.

110 g Triton ® X-100 were added per liter supernatant (tenside/protein ratio 55:1) and stirred for 30 minutes at 25° C. Factor VIII was then adsorbed on 750 ml DEAE-Toyopearl ® 650M by Tosohaas, equilibrated with buffer 1, in a column having a diameter of 9 cm at a pH of 6.8.

The factor VIII-containing fraction was eluted from the gel with 2.25 liter buffer 2 (a citrate-buffered 500 mM NaCl solution).

The specific activity was 76 IU factor VIII per mg protein.

After freezedrying of the ultrafiltered factor VIII-containing fraction, factor VIII was heated at 60° C. for 10 hours in a closed container with 7.5% w/w $H_2O$. The factor VIII activity was 72 % of the non-heated sample. Heat treatment in the presence of albumin led to a factor VIII activity of 92% of the non-heated sample.

Example 2

1 kg cryoprecipitate was obtained and dissolved in the same manner as in Example 1.

Prepurification was carried out with $Al(OH)_3$ and $BaSO_4$. To the supernatant, 120 g Tween ® 80 were added per liter (tenside/protein ratio 4:1) and stirred at 25° C. for 45 minutes. After dilution with buffer 1 at a ratio of 1:3, the solution was chromatographically purified by adsorption of factor VIII on 400 ml EMD-TMAE-Fractogel ® (Merck).

Before this, the gel was equilibrated with buffer 1. The non-bound proteins were separated by buffer 1, subsequently the factor VIII-containing fraction was eluted with buffer 2.

The specific activity was 45 IU factor VIII per mg protein.

The eluate was concentrated by ultrafiltration and freezedried. Factor VIII was heated at 60° C. for 10 hours in a closed container in the presence of 9.5% w/w $H_2O$.

The factor VIII activity was 87% of the non-heated sample.

The overall virus reduction factor according to the Directive EC III/8115/89-EN of the Commission of the European Community was determined by way of the example of HIV-1 and FSME viruses, virus suspension being added several times during this procedure. The overall virus reduction factor amounted to 12 at least. This corresponds to a reduction of the theoretical virus titer of at least $10^{12}$ over the entire procedure.

Example 3

The preparation comprising 3000 IU factor VIII produced according to Example 2 contained 120 U fibronectin (3,960 μg). To eliminate this impurity, the factor VIII-containing preparation was chromatographically purified by a 15 ml heparinsepharose column (diameter 1.6 cm) using a buffer of 260 mM NaCl.

Factor VIII was not bound, fibronectin was not detectable in the factor VIII-containing fraction. The specific activity was 46 IU factor VIII per mg protein. Fibronectin could be recovered by elution with 750 mM NaCl solution.

Example 4

1 kg cryoprecipitate was obtained and dissolved in the same manner as in Example 1. Prepurification was realized with Al(OH)$_3$ and PEG 4000.

0.15% Al(OH)$_3$ was added and stirred at 25° C. for 30 minutes. Al(OH)$_3$ was then separated by centrifugation and discarded. 3.15% PEG 4000 was added to the supernatant, the pH was adjusted to 6.6 and the temperature was lowered to 9° C. It was stirred for 30 minutes and the precipitate formed was separated by centrifugation and discarded.

Furthermore, 100 g Tween ® 80 were added to the supernatant per liter (tenside/protein ratio 50:1) and thoroughly mixed. After dilution with buffer 1 at a ratio of 1:3, the solution was chromatographed on 1.75 liter Q-Sepharose ® Fast Flow of Pharmacia.

Factor VIII was adsorbed and the unbound proteins were separated by means of 7.9 liter buffer 1. By elution with 5.25 liter of a sodium citrate-buffered 500 mM NaCl solution, a factor VIII-containing fraction was obtained.

The specific activity was 89 IU factor VIII per mg protein.

The concentrated eluate was lyophilized and subsequently was heated at 60° C. for 10 hours in the presence of 8% w/w H$_2$O in a closed vessel.

The factor VIII activity was 81% of the non-heated sample.

What we claim is:

1. A method of producing a virus-inactivated factor VIII preparation without using organic phosphate soluents, which method in combination comprises the steps of
    preparing a factor VIII-containing fraction, chromatographically purifying said factor VIII-containing fraction so as to obtain a factor VIII preparation,
    tenside-treating said factor VIII preparation in an aqueous solution at a tenside/protein ratio of from 1:1 to 1000:1 so as to obtain a tenside-treated factor VIII preparation, and
    heat-treating said tenside-treated factor VIII preparation in solid state.

2. A method according to claim 1, wherein heat-treating is effected with hot vapor by adjusting said tenside-treated factor VIII preparation in solid state to a content of one of water, methanol and ethanol of above 5% by mass and below 70% by mass and treating said tenside-treated factor VIII preparation in a closed container at a temperature ranging between 50° and 121° C.

3. A method according to claim 2, wherein said content of one of water, methanol and ethanol is adjusted to above 5% by mass and below 40% by mass.

4. A method according to claim 2, wherein an inert protective gas in said closed container is provided.

5. A method according to claim 1, wherein said chromatographically purifying said factor VIII-containing fraction employs a factor VIII adsorbing material and a material that adsorbs contaminating proteins.

6. A method according to claim 1, further comprising providing an anion exchanger for said chromatographically purifying said factor VIII-containing fraction, said anion exchanger being selected from the group consisting of acrylates, silicates and carbohydrates.

7. A method according to claim 6, wherein said anion exchanger is a matrix and comprises a polymer chain bound to said matrix, and wherein said polymer chain comprises anion exchange groups.

8. A method according to claim 1, wherein said virus-inactivated factor VIII has a specific activity of at least 25 U/mg protein.

9. A method of producing a virus-inactivated factor VIII preparation without using organic phosphate soluents, which method in combination comprises the steps of
    preparing a factor VIII-containing fraction,
    tenside-treating said factor VIII-containing fraction in an aqueous solution at a tenside/protein ratio of from 3.5:1 to 10:1 so as to obtain a tenside-treated factor VIII-containing fraction,
    chromatographically purifying said tenside-treated factor VIII-containing fraction so as to obtain a tenside-treated factor VIII preparation,
    heat-treating said tenside-treated factor VIII preparation in solid state.

10. A method according to claim 2, wherein heat-treating is effected with hot vapor by adjusting said tenside-treated factor VIII preparation in solid state to a content of one of water, methanol and ethanol of above 5% by mass and below 70% by mass and treating said tenside-treated factor VIII preparation in a closed container at a temperature ranging between 50° and 121° C.

11. A method according to claim 9, wherein said chromatographically purifying said factor VIII-containing fraction is effected in several steps comprising a step using a factor VIII adsorbing material and a step using a contaminating protein adsorbing material.

12. A method according to claim 2, further comprising providing an anion exchanger for said chromatographically purifying said factor VIII-containing fraction, said anion exchanger being selected from the group consisting of acrylates, silicates and carbohydrates.

13. A method according to claim 2, wherein said virus-inactivated factor VIII has a specific activity of at least 25 U/mg protein.

14. A method of producing a virus-inactivated factor VIII preparation without using organic phosphate soluents, which method in combination comprises the steps of
    preparing a factor VIII-containing fraction, tenside-treating said factor VIII-containing fraction in an aqueous solution at a tenside/protein ratio of from 1:1 to 1000:1 while chromatographically purifying said factor VIII-containing fraction so as to obtain a tenside-treated factor VIII preparation, heat-treating said tenside-treated factor VIII preparation in solid state.

15. A method according to claim 14, wherein heat-treating is effected with hot vapor by adjusting said tenside-treated factor VIII preparation in solid state to a content of one of water, methanol and ethanol of above 5% by mass and below 70% by mass and treating said tenside-treated factor VIII preparation in a closed container at a temperature ranging between 50° and 121° C.

16. A method according to claim 14, wherein said chromatographically purifying said factor VIII-containing fraction is effected in several steps comprising a step using a factor VIII adsorbing material and a step using a contaminating protein adsorbing material.

17. A method according to claim 3, further comprising providing an anion exchanger for said chromatographically purifying said factor VIII-containing fraction, said anion exchanger being selected from the group consisting of acrylates, silicates and carbohydrates.

18. A method according to claim 3, wherein said virus-inactivated factor VIII has a specific activity of at least 25 U/mg protein.

19. A method of producing a virus inactivated factor VIII preparation without using organic phosphate solvents, comprising the steps of:
    preparing a factor VIII containing fraction,
    contacting said fraction containing factor VIII with a tenside in an aqueous solution,
    purifying chromatographically the fraction containing factor VIII, and
    heating in a solid state factor VIII from said purifying and contacting steps.

20. A method according to claim 19, wherein said contacting step is conducted prior to said purifying step.

21. A method according to claim 19, wherein said purifying step is conducted prior to said contacting step.

22. A method according to claim 19, wherein said purifying step is conducted concurrently with said contacting step.

23. A method according to claim 19, wherein said tenside is present in a tenside/protein ratio ranging from 1:1 to 1000:1.

24. A method according to claim 19, wherein said fraction containing factor VIII is in a wet solid state during said heating step.

25. A method according to claim 24, wherein during the heating step said fraction containing factor VIII contains 5 to 70% by mass water, methanol or ethanol.

26. A method according to claim 19, wherein said purifying step is performed with an anion exchange column.

* * * * *